(12) United States Patent
Bouhadir et al.

(10) Patent No.: US 11,878,036 B2
(45) Date of Patent: Jan. 23, 2024

(54) VAGINAL CARE COMPOSITIONS AND METHODS OF IMPROVING VAGINAL HEALTH

(71) Applicant: Neuvian LLC, St. Petersburg, FL (US)

(72) Inventors: Spencer Bouhadir, Lake Worth, FL (US); Jacob Miguel, Miami, FL (US)

(73) Assignee: NEUVIAN LLC, St. Petersburg, FL (US)

( * ) Notice: Subject to any disclaimer, the term of this patent is extended or adjusted under 35 U.S.C. 154(b) by 0 days.

(21) Appl. No.: 18/321,644

(22) Filed: May 22, 2023

(65) Prior Publication Data
US 2023/0381242 A1  Nov. 30, 2023

Related U.S. Application Data

(60) Provisional application No. 63/345,685, filed on May 25, 2022.

(51) Int. Cl.
| | | |
|---|---|---|
| A61K 35/32 | (2015.01) | |
| A61K 35/12 | (2015.01) | |
| A61K 35/35 | (2015.01) | |
| A61K 35/407 | (2015.01) | |
| A61K 35/42 | (2015.01) | |
| A61K 35/50 | (2015.01) | |
| A61K 35/51 | (2015.01) | |
| A61K 9/00 | (2006.01) | |
| A61K 9/16 | (2006.01) | |
| A61K 9/48 | (2006.01) | |
| A61K 31/4172 | (2006.01) | |
| A61K 45/06 | (2006.01) | |
| A61K 47/02 | (2006.01) | |
| A61P 15/00 | (2006.01) | |
| A61P 15/02 | (2006.01) | |

(52) U.S. Cl.
CPC ............ *A61K 35/32* (2013.01); *A61K 9/0034* (2013.01); *A61K 9/1611* (2013.01); *A61K 9/1658* (2013.01); *A61K 9/1664* (2013.01); *A61K 9/485* (2013.01); *A61K 9/4833* (2013.01); *A61K 9/4858* (2013.01); *A61K 9/4866* (2013.01); *A61K 9/4875* (2013.01); *A61K 31/4172* (2013.01); *A61K 35/12* (2013.01); *A61K 35/35* (2013.01); *A61K 35/407* (2013.01); *A61K 35/42* (2013.01); *A61K 35/50* (2013.01); *A61K 35/51* (2013.01); *A61K 45/06* (2013.01); *A61K 47/02* (2013.01); *A61P 15/00* (2018.01); *A61P 15/02* (2018.01)

(58) Field of Classification Search
None
See application file for complete search history.

(56) References Cited

U.S. PATENT DOCUMENTS

| | | | |
|---|---|---|---|
| 10,265,348 B2 | 4/2019 | Soley Astals et al. | |
| 10,512,603 B2 | 12/2019 | Domènech et al. | |
| 2003/0113370 A1* | 6/2003 | Firestone | G16H 20/10 424/452 |
| 2010/0126521 A1* | 5/2010 | Kyte, III | A61K 8/046 514/552 |
| 2020/0069802 A1* | 3/2020 | Xiong | A61K 38/26 |
| 2020/0121722 A1 | 4/2020 | Yl et al. | |
| 2022/0233508 A1* | 7/2022 | Kandula | A61K 31/167 |
| 2023/0117663 A1* | 4/2023 | Plews | A61K 8/14 424/401 |

FOREIGN PATENT DOCUMENTS

| | | | | |
|---|---|---|---|---|
| CN | 1376051 A | * | 10/2002 | ............ A61K 8/361 |
| CN | 109330964 A | * | 2/2019 | |
| CN | 110339147 A | | 10/2019 | |
| CN | 112315979 A | | 2/2021 | |
| CN | 112516067 A | | 3/2021 | |
| CN | 114480273 A | | 5/2022 | |
| DE | 29522375 U1 | * | 8/2002 | ............ A61K 31/19 |
| KR | 20180105625 A | * | 9/2018 | |
| WO | WO-2017/122095 A1 | | 7/2017 | |
| WO | WO-2020/018926 A1 | | 1/2020 | |
| WO | WO-2020/130800 A1 | | 6/2020 | |
| WO | WO-2020/214100 A2 | | 10/2020 | |
| WO | WO-2021/216903 A1 | | 10/2021 | |
| WO | WO-2022026622 A2 | * | 2/2022 | |
| WO | WO-2022/245861 A1 | | 11/2022 | |
| WO | WO-2023/283578 A1 | | 1/2023 | |

OTHER PUBLICATIONS

English translation for CN-109330964A (2019).*
English translation for the claims of DE 295 22 375 U1 (2002).*
English translation for KR-20180105625A (2018).*
English translation for CN 1376051A (2002).*
Olson ("Vaginal Suppositories: What They Are & How to Use Them", an internet article found at the website: https://www.intimaterose.com/blogs/womens-health/vaginal-suppositories) (date unknown).*

(Continued)

*Primary Examiner* — Sin J Lee
(74) *Attorney, Agent, or Firm* — FOLEY & LARDNER LLP

(57) ABSTRACT

The instant disclosure is directed to a vaginal care composition that restores pH balance, and thereby reduces vaginal dryness, irritation, dyspareunia, post-coital bleeding, infections, vaginal and pelvic pain and increases vaginal lubrication. In some embodiments, the vaginal care composition comprises stem cell-derived exosomes (e.g., mesenchymal stem cell (MSC)-derived exosomes), an antioxidant and a pH buffer. Another aspect of the disclosure is directed to methods for improving vaginal health by administering the vaginal care composition of the instant disclosure.

18 Claims, 3 Drawing Sheets

(56) References Cited

OTHER PUBLICATIONS

Liu, Xiaochun, et al., "Exosomes secreted by adipose-derived mesenchymal stem cells regulate type I collagen metabolism in fibroblasts from women with stress urinary incontinence," Stem Cell Research & Therapy, (2018) 9:159, https://doi.org/10.1186/s13287-018-0899-9.

Zhu, Zhongyi, et al., "Exosomes derived from human umbilical cord mesenchymal stem cells accelerate growth of VK2 vaginal epithelial cells through MicroRNAs in vitro", Human Reproduction, vol. 34, No. 2, pp. 248-260, 2019.

International Search Report dated Aug. 30, 2023 issued in International Application No. PCT/US2023/023086, 6 pages.

Written Opinion of the International Searching Authority dated Aug. 30, 2023 issued in International Application No. PCT/US2023/023086, 10 pages.

\* cited by examiner

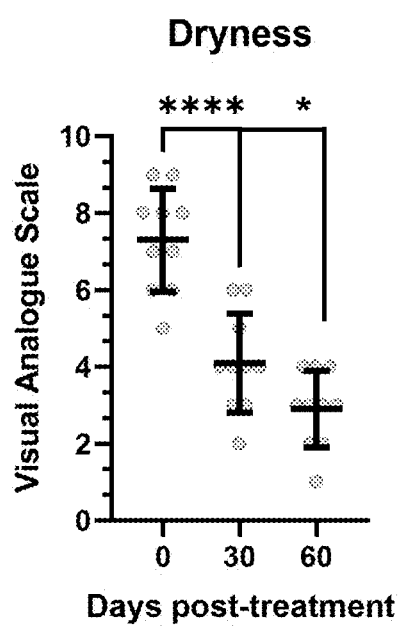
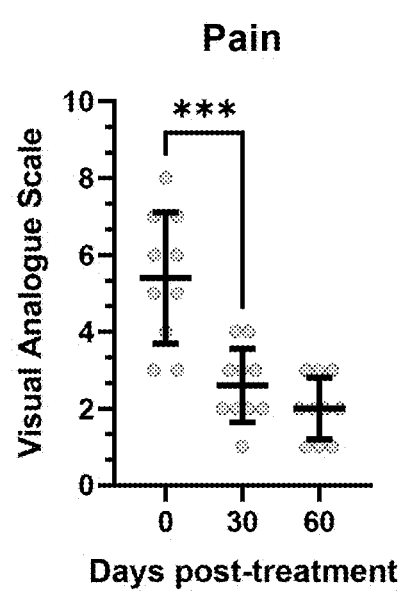
FIG. 3A                    FIG. 3B

US 11,878,036 B2

VAGINAL CARE COMPOSITIONS AND METHODS OF IMPROVING VAGINAL HEALTH

CROSS REFERENCE TO RELATED APPLICATION

This application claims the benefit of and priority to U.S. Application No. 63/345,685 filed May 25, 2022, which is incorporated herein by reference in its entirety.

BACKGROUND

As women age, their vaginal health declines. Many issues surface, primarily due to hormonal level changes. Specifically, estrogen levels drop significantly causing fat and collagen loss, decreased blood flow, bladder atrophy, orgasmic dysfunction, and reduced sensitivity, amongst other problems.

Genitourinary syndrome of menopause (GSM) is the broad term for vulvovaginal atrophy, atrophic vaginitis, or urogenital atrophy due to a lack of estrogen production that occurs with aging. GSM is a chronic progressive disorder that does not just occur during menopause, hence affecting some 15% of women that are premenopausal. GSM affects some 50-70% of women with many being undiagnosed due to the reluctance of women to report any of the symptoms because of embarrassment. Some of the key signs and symptoms of GSM include vaginal dryness, irritation, dyspareunia, reduced lubrication, post-coital bleeding, decreased arousal, infections, vaginal and pelvic pain. Vaginal dryness may be the most prevalent, affecting up to 93% of women. When not addressed, these problems can significantly affect the quality of life for those suffering from GSM, especially those that are sexually active.

Diagnoses of GSM may be rather challenging for women having mild to moderate symptoms. Clinicians most commonly diagnose the problem when women presented with dyspareunia secondary to vaginal dryness. This may happen as women are pre, peri or post-menopausal. There are multiple variables that cause this problem indirectly due to lack of appropriate estrogen production. With decreased estrogen, the vagina has diminished collagen, elastin and hyaluronic acid production as the epithelium thins, which causes a loss in labial and vulval thickness, reduced vaginal discharge and dryness. Moreover, there is a loss of vasculature and impaired smooth muscle proliferation. Ultimately, lack of vasculature can cause sexual intercourse pain (dyspareunia), atrophy, cramping amongst other painful problems.

Further, loss of estrogen leads to a reduction in *Lactobacillus* which can make the vaginal fluid more basic. This higher pH throws off the balance of healthy flora within the vagina and can promote overgrowth of less favorable bacterial flora causing vaginal infections, urinary tract infections, inflammation and pain.

Addressing GSM with the use of estrogen is the most common first approach. Exogenous estrogen comes with many side effects, which include excess bleeding or spotting, breast tenderness and/or enlargement, nausea, and weight gain. In many cases, women do not tolerate exogenous estrogen or are not a candidate for it due to suspected breast or estrogen-dependent cancers, history of blood clotting disorders, endometriosis, hypertension, and hyperlipidemia, amongst other diseases. Some women are not even receptive to the use of estrogen.

Therefore, there is a need for targeting pre, peri and post-menopausal vaginal conditions and improving vaginal health in general. At a minimum, targeting dryness, sensation and imbalanced pH, will improve the quality of life for those women suffering from these problems and GSM. Considering the potential side effects of estrogen and steroid treatments, there is a great need for non-steroidal treatments for vaginal health issues.

SUMMARY OF THE INVENTION

An aspect of the disclosure is directed to a vaginal care composition that restores pH balance, and thereby reduces vaginal dryness, irritation, dyspareunia, post-coital bleeding, infections, vaginal and pelvic pain and increases vaginal lubrication. In some embodiments, the vaginal care composition comprises stem cell-derived exosomes (e.g., mesenchymal stem cell (MSC)-derived exosomes), an antioxidant, and a pH buffer.

In some embodiments, the vaginal care composition comprises, by weight of the total composition: (a) 1%-50% exosomes (e.g., stem cell-derived exosomes or MSC-derived exosomes), (b) 10%-25% antioxidant, and (c) a pH buffer. In some embodiments, the pH of the vaginal care composition is between pH 3.5 and pH 7, between pH 4.5 and pH 6.5, between pH 4.5 and pH 5.0, between pH 5.0 and pH 5.5, between pH 5.5 and pH 6.0, or between pH 6.0 and pH 6.5.

In some embodiments, the exosomes comprise mesenchymal stem cell (MSC)-derived exosomes.

In some embodiments, the vaginal care composition comprises between 5%-40%, between 10%-30%, or between 15%-25% stem cell-derived exosomes. In some embodiments, the vaginal care composition comprises between 5%-40%, between 10%-30%, or between 15%-25% MSC-derived exosomes.

In some embodiments, the vaginal care composition comprises between 10%-15%, between 15%-20%, or between 10%-20% antioxidant.

In some embodiments, the vaginal care composition comprises between 30%-40%, between 25%-45%, between 25%-35%, between 25%-50%, or between 25%-75% pH buffer.

In some embodiments, the antioxidant is selected from L-carnosine, D-carnosine, acetyl-carnosine, anserine, alanine, L-histidine, and D-histidine. In some embodiments, the antioxidant comprises L-carnosine.

In some embodiments, the pH buffer is selected from magnesium citrate, magnesium sulfate, sodium citrate, and sodium sulfate. In some embodiments, the pH buffer comprises magnesium citrate.

In some embodiments, the vaginal care composition further comprises at least one of the following constituents: *Lactobacillus bifidus, Saccharomyces cerevisiae*, vitamin A, D-alpha-tocopherol, pantothenate, zinc, selenium, or oligofructose.

In some embodiments, the vaginal care composition further comprises at least one of the following constituents: sunflower oil, Tegomuls 90 S, cetyl alcohol, cetaceum artificiale, Polysorbate 80, methyl 4-hydroxybenzoate, propyl 4-hydroxybenzoate, sesame oil, wool wax, yellow wax, wool wax alcohols, glycerol, glycerol ester, palmitic acid ester, vaseline, cocoa butter, liquid wax, olive oil or distilled water.

In some embodiments, the vaginal care composition further comprises at least one of the following constituents: an antibiotic agent, a free radical generating agent, an antifungal agent, an antiviral agent, a nucleoside-analog reverse transcriptase inhibitor, a non-nucleoside reverse transcriptase inhibitor, a protease inhibitor, an immunosuppressant, an anti-inflammatory agent, a retinoid agent, a tar agent, an antihistamine agent, and an antipruritic agent.

In some embodiments, the vaginal care composition is a capsule, an ovule, a cream, an ointment or a tampon. In some embodiments, the vaginal care composition is a capsule for intra-vaginal administration, wherein the capsule comprises 5-100 mg, 5-10 mg, 10-20 mg, 20-50 mg, or 50-100 mg of MSC-derived exosomes. In some embodiments, the vaginal care composition comprises MSC-derived exosomes, L-carnosine as the antioxidant, and magnesium citrate as the pH buffer.

Another aspect of the disclosure is directed to a method for improving vaginal health in a subject, comprising administering to the subject in need thereof a vaginal care composition comprising stem cell-derived exosomes (e.g., mesenchymal stem cell (MSC)-derived exosomes), an antioxidant and a pH buffer.

In some embodiments, the vaginal care composition comprises, by weight of the total composition: (a) 1%-50% exosomes (e.g., stem cell-derived exosomes or MSC-derived exosomes), (b) 10%-25% antioxidant, and (c) a pH buffer. In some embodiments, the pH of the composition is between pH 3.5 and pH 7, between pH 4.5 and pH 6.5, between pH 4.5 and pH 5.0, between pH 5.0 and pH 5.5, between pH 5.5 and pH 6.0, or between pH 6.0 and pH 6.5.

In some embodiments, the exosomes comprise mesenchymal stem cell (MSC)-derived exosomes.

In some embodiments, the composition comprises between 5%-40%, between 10%-30%, or between 15%-25% stem cell-derived exosomes. In some embodiments, the composition comprises between 5%-40%, between 10%-30%, or between 15%-25% MSC-derived exosomes.

In some embodiments, the composition comprises between 10%-15%, between 15%-20%, or between 10%-20% antioxidant.

In some embodiments, the composition comprises between 30%-40%, between 25%-45%, between 25%-35%, between 25%-50%, or between 25%-75% pH buffer.

In some embodiments, the antioxidant is selected from L-carnosine, D-carnosine, acetyl-carnosine, anserine, alanine, L-histidine, and D-histidine. In some embodiments, the antioxidant comprises L-carnosine.

In some embodiments, the pH buffer is selected from magnesium citrate, magnesium sulfate, sodium citrate, and sodium sulfate. In some embodiments, the pH buffer comprises magnesium citrate.

In some embodiments, the vaginal care composition further comprises at least one of the following constituents: *Lactobacillus bifidus, Saccharomyces cerevisiae*, vitamin A, D-alpha-tocopherol, pantothenate, zinc, selenium, or oligofructose.

In some embodiments, the vaginal care composition further comprises at least one of the following constituents: sunflower oil, Tegomuls 90 S, cetyl alcohol, cetaceum artificiale, Polysorbate 80, methyl 4-hydroxybenzoate, propyl 4-hydroxybenzoate, sesame oil, wool wax, yellow wax, wool wax alcohols, glycerol, glycerol ester, palmitic acid ester, vaseline, cocoa butter, liquid wax, olive oil or distilled water.

In some embodiments, the vaginal care composition further comprises at least one of the following constituents: an antibiotic agent, a free radical generating agent, an antifungal agent, an antiviral agent, a nucleoside-analog reverse transcriptase inhibitor, a non-nucleoside reverse transcriptase inhibitor, a protease inhibitor, an immunosuppressant, an anti-inflammatory agent, a retinoid agent, a tar agent, an antihistamine agent, and an antipruritic agent.

In some embodiments, the composition is a capsule, an ovule, a cream, an ointment or a tampon. In some embodiments, the vaginal care composition is a capsule for intra-vaginal administration, wherein the capsule comprises 5-100 mg, 5-10 mg, 10-20 mg, 20-50 mg, or 50-100 mg of MSC-derived exosomes. In some embodiments, the vaginal care composition comprises MSC-derived exosomes, L-carnosine as the antioxidant, and magnesium citrate as the pH buffer.

In some embodiments, the composition is administered intra-vaginally. In some embodiments, the composition is administered every hour, every two hours, every three hours, every six hours, every twelve hours, every day, every two days, every three days, every five days, every seven days, every ten days, or every fourteen days. In some embodiments, the vaginal care composition is a capsule for intra-vaginal administration; wherein the capsule comprises 5-100 mg MSC-derived exosomes, L-carnosine, and magnesium citrate; and wherein the subject receives one capsule every week. In some embodiments, the vaginal care composition is a capsule for intra-vaginal administration; wherein the capsule comprises 5-100 mg MSC-derived exosomes, L-carnosine, and magnesium citrate; and wherein the subject receives two capsules every week. In some embodiments, the vaginal care composition is a capsule for intra-vaginal administration; wherein the capsule comprises 5-100 mg MSC-derived exosomes, L-carnosine, and magnesium citrate; and wherein the subject receives three capsules every week.

In some embodiments, the subject has been suffering from at least one of the following: vaginal dryness, irritation, dyspareunia, reduced lubrication, post-coital bleeding, decreased arousal, infections, vaginal or pelvic pain. In some embodiments, the vaginal care composition reduces the vaginal pH of the subject by at least 0.5, at least 1.0, or at least 1.5, after 30 days of treatment. In some embodiments, the vaginal care composition reduces the vaginal pH of the subject by at least 0.5, at least 1.0, at least 1.5, or at least 2.0, after 60 days of treatment.

BRIEF DESCRIPTION OF THE DRAWINGS

FIGS. 3A-3B. (A) Bar graph showing vaginal dryness measured by Yale Visual Analogue Scale as reported by participating women. (B) Bar graph showing vaginal pain measured by Yale Visual Analogue Scale as reported by participating women. Each circle represents one patient (n=10). Mean±SD. ****p<0.0001 for 0 vs 30; *p=0.03 for 30 vs 60 by two-tailed t test, ***p=0.0003.

DETAILED DESCRIPTION

Definitions

Figure 1:
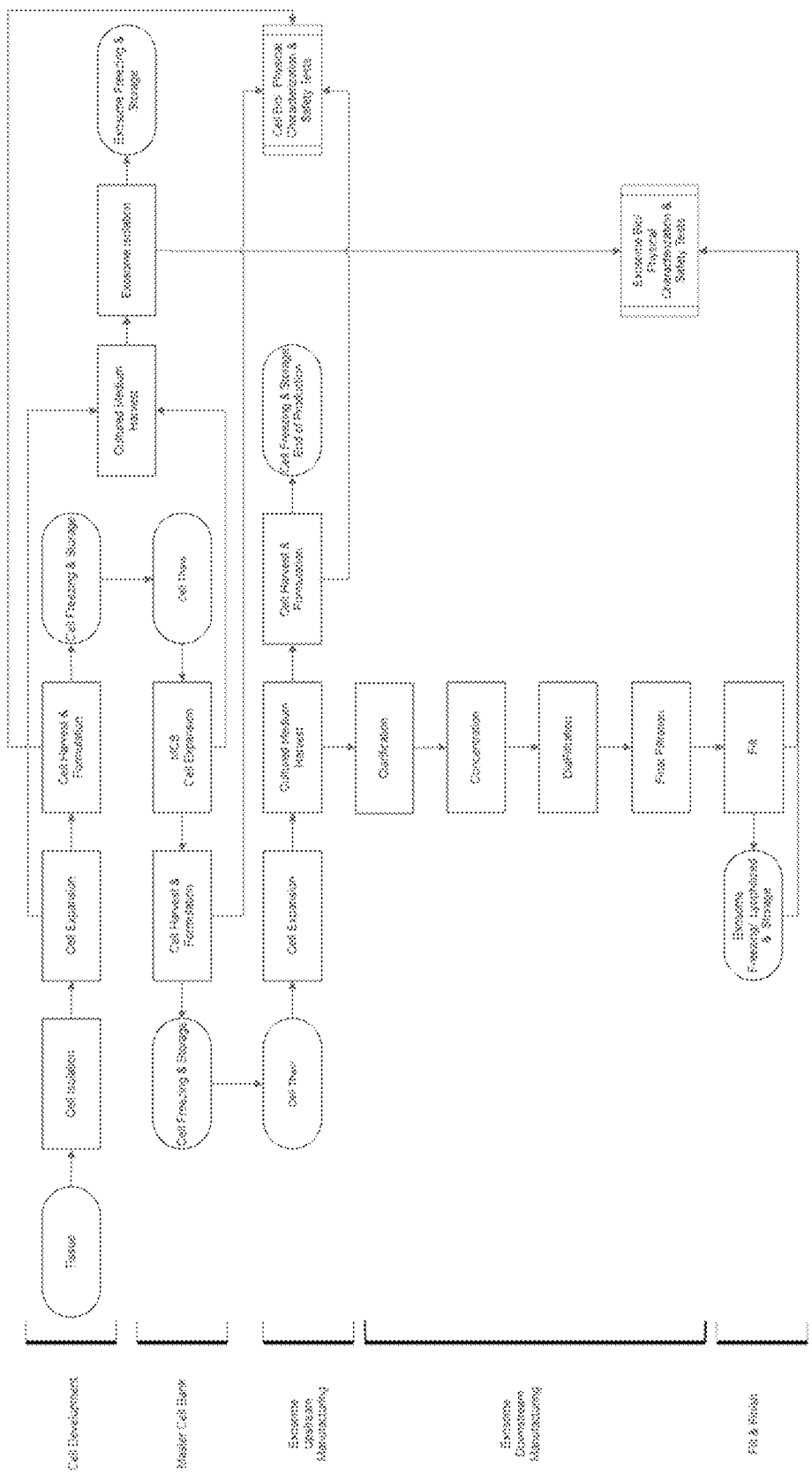
FIG. 1. A schematic representation of an exemplary process for producing mesenchymal stem cell (MSC)-derived exosomes.

Unless otherwise defined, all technical and scientific terms used herein have the same meaning as commonly understood by one of ordinary skill in the art to which the present technology belongs.

As used herein, unless otherwise stated, the singular forms "a," "an," and "the" encompasses plural reference. Thus, for example, a reference to "a molecule" encompasses a plurality of molecules.

As used herein, the term "about" in reference to a number is generally taken to encompass numbers that fall within a range of 1%-10% in either direction (greater than or less than) of the number unless otherwise stated or otherwise evident from the context.

As used here, the term "or" is generally employed in its usual sense including "and/or" unless the content clearly dictates otherwise. The term "and/or" encompasses one or all of the listed elements or a combination of two or more of the listed elements.

Any amounts (e.g., concentrations) of components in a composition given as a percentage (%) encompasses a percentage by weight (wt. %) or a percentage by volume (vol. %) unless otherwise indicated.

A "composition" encompasses a combination of active agents, such as exosomes (e.g., MSC-derived exosomes) as disclosed herein, and another compound or composition, inert or active, such as an antioxidant (e.g., L-carnosine, D-carnosine, acetyl-carnosine, anserine, alanine, L-histidine, D-histidine) and a PH buffer (e.g., magnesium citrate, magnesium sulfate, sodium citrate, sodium sulfate), and optionally an adjuvant, diluent, binder, stabilizer, buffers, salts, lipophilic solvents, preservative, or the like and include pharmaceutically acceptable carriers.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton). The term pharmaceutically acceptable carrier (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present disclosure include liquids, semi-solid (e.g., gels) and solid materials (e.g., cell scaffolds and matrices, tube sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

"Pharmaceutically acceptable carriers" encompasses any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

The term "preservative" encompasses pharmaceutically acceptable excipients which prevent the growth of microorganisms within the composition and protects the composition against microbial contamination. Exemplified preservatives include a number of organic acids and their salts, such as lactic acid and lactates, propionic acid and propionates, citric acid, acetic acid, sorbic acid, and sorbates, benzoic acid and benzoates, and methyl and propyl parabens (benzoic acid derivatives). Other preservatives are also used, for example, Dandlin et al. Sci Rep. 2017 Jul. 18; 7(1):5658.

"Administration" or "delivery" of a vaginal care composition of the instant disclosure encompasses in vivo administration or delivery and can be performed in one dose, continuously or intermittently throughout the course of treatment. The most effective means and dosage of administration can be determined according to the composition used for therapy, the purpose of the therapy, the target cell being treated, and the subject being treated. Single or multiple administrations can be carried out with the dose level and pattern being selected by the treating physician or in the case of animals, by the treating veterinarian. Suitable dosage formulations and methods of administering the agents are known in the art. The most effective route of administration can be determined according to the composition used for treatment, the purpose of the treatment, the health condition or disease stage of the subject being treated, and target cell or tissue. The preferred route of administration for the vaginal care compositions is intra-vaginal administration. In some embodiments, the administration of the vaginal care compositions is a timed release over a certain period of time, such as over about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours, about 2 days, about 3 days, about 4 days, about 5 days, about 6 days, about 7 days, or longer. In some embodiments, $1 \times 10^4$ to $1 \times 10^{15}$ exosomes as disclosed herein as a vaginal care composition are administrated to a subject, such as $1 \times 10^7$ to $1 \times 10^{10}$ exosomes per administration, $1 \times 10^4$ to $1 \times 10^5$ exosomes per administration, $1 \times 10^5$ to $1 \times 10^6$ exosomes per administration, $1 \times 10^6$ to $1 \times 10^7$ exosomes per administration, $1 \times 10^7$ to $1 \times 10^8$ exosomes per administration, $1\times10^8$ to $1\times10^9$ exosomes per administration, $1\times10^9$ to $1\times10^{10}$ exosomes per administration, $1\times10^{10}$ to $1\times10^{11}$ exosomes per administration, $1\times10^{11}$ to $1\times10^{12}$ exosomes per administration, $1\times10^{12}$ to $1\times10^{13}$ exosomes per administration, $1\times10^{13}$ to $1\times10^{14}$ exosomes per administration. In some embodiments, administration or delivery of a vaginal care composition of the instant disclosure can also be performed in a plurality of doses with certain intervals. In some embodiments, the intervals can be 1 day, 2 days, 3 days, 4 days, 5 days, 6 days, 1 week, 10 days, 2 weeks, 3 weeks, 1 month, 2 months, 3 months, 4 months, 5 months, 6 months, 1 year or longer. In some embodiments, one dose is repeated for once, twice, three times, four times, five times, six times, seven times, eight times, nine times, ten times or more. For example, cells as disclosed herein may be administered to a subject weekly and for up to four weeks. The compositions and therapies can be combined with other suitable therapies such as steroid administration or probiotic bacteria administration.

An "effective amount" encompasses an amount sufficient to effect beneficial or desired results. An effective amount can be administered in one or more administrations, applications or dosages. Such delivery is dependent on a number of variables including the time period for which the therapeutic agent is to be used, the bioavailability of the therapeutic agent, the route of administration, etc. It is understood, however, that specific dosage levels of the therapeutic agents of the present disclosure for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro, or ex vivo, or in vivo tests (or any combination thereof) initially can provide useful guidance on the proper doses for patient administration. In general, one will desire to administer an amount of the agent as disclosed herein (such as a cell) that is effective to achieve a serum level commensurate with the concentrations found to be effective in vitro or ex vivo.

"Therapeutically effective amount" of a drug or an agent encompasses an amount of the drug or the agent (such as a vaginal acre composition as disclosed herein) that is an amount sufficient to obtain a pharmacological response; or alternatively, is an amount of the drug or agent that, when administered to a patient with a specified disorder or disease, is sufficient to have the intended effect, e.g., treatment, alleviation, amelioration, palliation or elimination of one or more manifestations of the specified disorder or disease in the patient. A therapeutic effect does not necessarily occur by administration of one dose, and may occur only after administration of a series of doses, as needed to induce a partial or complete effect. Thus, a therapeutically effective amount may be administered in one or more administrations. In some embodiments, a therapeutically effective amount of exosomes as disclosed herein is $1\times10^4$ to $1\times10^{15}$ or ranges, such as $1\times10^7$ to $1\times10^{10}$.

As used herein, the term "cryopreservation" refers to storage of cells or tissue in an environment of less than about 8° C., which allows for extended storage of cells and can be at any temperature below 8° C., including temperatures at or below 4° C., 0° C., −20° C., −70° C., −80° C., −135° C., or in liquid nitrogen (−196° C.). Methods for cryopreserving cells with a medium containing choline salts and sucrose is disclosed in U.S. Pat. No. 5,985,538, which is incorporated herein by reference in its entirety. Additional cryopreservation compositions and methods are disclosed in U.S. Pat. Nos. 7,935,478, 7,112,576 and US Application No. 20170198251A1, which are incorporated herein by reference in their entireties.

As used herein, the terms "cryoprotectant" and "cryoprotective agent" refer to a substance that prevents or reduces damage to cells during cryopreservation. Exemplified cryoprotective agents include a sugar (such as sucrose, dextrose, trehalose, pectin), glycerol, ethylene glycol, propylene glycol, polyethylene glycol (PEG), 1,2-propanediol, trehalose, carbohydrates (such as hydroxy ethyl starch (HES)), dextran, polylysine and dimethyl sulfoxide (DMSO).

As used herein, the term "lyophilization" (also known as "lyophilizing," "freeze drying" or "cryodessication") refers to a low temperature dehydration process that involves freezing a product and lowering pressure, and removing the ice by sublimation. Lyophilizing may comprise freezing the composition at a temperature of, e.g. greater than −40° C. or less than −30° C., forming a frozen composition, and drying the frozen composition to form the lyophilized composition. The step of drying may occur at 50 mTorr at a temperature of −25 to −34° C., or −30 to −34° C.

As used herein, the term "lyoprotection" refers to stabilization during all of the freeze-drying process (i.e., during both freezing and drying). Such stabilization is often required for freeze-drying of biological materials such as proteins, peptides and biological drugs. This is because complex biological molecules often require a moderate level of residual water to maintain structure and function. Accordingly, a "lyoprotectant" protects the structure and/or function of biologic drugs during lyophilization (e.g., prevents aggregation, improves bioavailability, increases stability and/or improves membrane integrity and cargo retention).

Exemplary lyoprotectants include sugars such as sucrose or trehalose; an amino acid such as monosodium glutamate or histidine; a methylamine such as betaine; a lyotropic salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In one embodiment, a lyoprotectant is a non-reducing sugar, such as trehalose or sucrose. Other exemplary lyoprotectants are disclosed in U.S. patent Ser. No. 10/821,138, which is incorporated herein by reference in its entirety.

In some embodiments, the lyoprotectant is effective at protecting biological activity and/or structural integrity of exosomes in the instant vaginal care compositions at least 90%, 91%, 92%, 93%, 94%, 95%, 96%, 97%, 98%, 99% or more as compared to exosomes that have not been lyophilized. In addition, the lyoprotectant increases the stability of lyophilized exosomes during storage (which can be room temperature (about 25° C.), 4° C., or −20° C., or any value therebetween). In some embodiments, the lyoprotectant also increases both the stability and potency of the vaginal care composition.

As used herein, the terms "individual", "patient", or "subject" encompass an individual organism, a vertebrate, a mammal, or a human. In some embodiments, the individual, patient or subject is a human.

Vaginal Care Compositions

An aspect of the disclosure is directed to a vaginal care composition that restores pH balance, and thereby reduces vaginal dryness, irritation, dyspareunia, post-coital bleeding, infections, vaginal and pelvic pain and increases vaginal lubrication. In some embodiments, the vaginal care composition comprises exosomes, an antioxidant, and a pH buffer.

In some embodiments, the vaginal care composition comprises stem cell-derived exosomes (e.g., mesenchymal stem cell (MSC)-derived exosomes), an antioxidant, and a pH buffer.

In some embodiments, the vaginal care composition comprises, by weight of the total composition:
(a) 1%-50% (e.g., 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%) exosomes (e.g., stem cell-derived exosomes such as MSC-derived exosomes),
(b) 10%-25% (e.g., 10%, 11%, 12%, 13%, 14%, 15%, 16%, 17%, 18%, 19%, 20%, 21%, 22%, 23%, 24%, or 25%) antioxidant, and
(c) a pH buffer.

In some embodiments, the vaginal care composition comprises, by weight of the total composition:
(a) 1%-50% (e.g., 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%) exosomes (e.g., stem cell-derived exosomes such as MSC-derived exosomes),
(b) 10%-25% (e.g., 10%, 11%, 12%, 13%, 14%, 15%, 16%, 17%, 18%, 19%, 20%, 21%, 22%, 23%, 24%, or 25%) antioxidant, and
(c) 25%-50% (e.g., 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%) pH buffer.

In some embodiments, the vaginal care composition comprises, by weight of the total composition:
(a) 1%-40% (e.g., 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40%) exosomes (e.g., stem cell-derived exosomes such as MSC-derived exosomes),
(b) 10%-20% (e.g., 10%, 11%, 12%, 13%, 14%, 15%, 16%, 17%, 18%, 19%, or 20%) antioxidant, and
(c) 25%-75% (e.g., 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%) pH buffer.

In some embodiments, the vaginal care composition comprises, by weight of the total composition:
(a) 1%-30% (e.g., 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, 25%, 26%, 27%, 28%, 29%, or 30%) exosomes (e.g., stem cell-derived exosomes such as MSC-derived exosomes),
(b) 10%-25% (e.g., 10%, 11%, 12%, 13%, 14%, 15%, 16%, 17%, 18%, 19%, 20%, 21%, 22%, 23%, 24%, or 25%) antioxidant, and
(c) 35%-75% (e.g., 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%) pH buffer.

In some embodiments, the vaginal care composition comprises, by weight of the total composition:
(a) 1%-10% (e.g., 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%) exosomes (e.g., stem cell-derived exosomes such as MSC-derived exosomes),
(b) 15%-25% (e.g., 15%, 16%, 17%, 18%, 19%, 20%, 21%, 22%, 23%, 24%, or 25%) antioxidant, and
(c) 55%-75% (e.g., 55%, 56%, 57%, 58%, 59%, 60%, 61%, 62%, 63%, 64%, 65%, 66%, 67%, 68%, 69%, 70%, 71%, 72%, 73%, 74%, or 75%) pH buffer.

In some embodiments, the vaginal care composition comprises, by weight of the total composition:
(a) 5%-10% (e.g., 5%, 5.5%, 6%, 6.5%, 7%, 7.5%, 8%, 8.5%, 9%, 9.5%, or 10%) exosomes (e.g., stem cell-derived exosomes such as MSC-derived exosomes),
(b) 15%-20% (e.g., 15%, 16%, 17%, 18%, 19%, or 20%) antioxidant, and
(c) 25%-30% (e.g., 25%, 26%, 27%, 28%, 29%, or 30%) pH buffer.

In some embodiments, the vaginal care composition comprises, by weight of the total composition:
(a) 5%-10% (e.g., 5%, 5.5%, 6%, 6.5%, 7%, 7.5%, 8%, 8.5%, 9%, 9.5%, or 10%) exosomes (e.g., stem cell-derived exosomes such as MSC-derived exosomes),
(b) 15%-20% (e.g., 15%, 16%, 17%, 18%, 19%, or 20%) antioxidant, and
(c) 55%-80% (e.g., 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80%) pH buffer.

In some embodiments, the vaginal care composition comprises, by weight of the total composition:
(a) 0.05%-1% (e.g., 0.05%, 0.07%, 0.1%, 0.2%, 0.3%, 0.4%, 0.5%, 0.6%, 0.7%, 0.9%, or 1%) exosomes (e.g., stem cell-derived exosomes such as MSC-derived exosomes),
(b) 15%-20% (e.g., 15%, 16%, 17%, 18%, 19%, or 20%) antioxidant, and
(c) 55%-80% (e.g., 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80%) pH buffer.

In a specific embodiment, the vaginal care composition comprises, by weight of the total composition:
exosomes),
(a) 5% exosomes (e.g., stem cell-derived exosomes such as MSC-derived
(b) 20% antioxidant, and
(c) 60-75% (60%, 61%, 62%, 63%, 64%, 65%, 66%, 67%, 68%, 69%, 70%, 71%, 72%, 73%, 74%, or 75%) pH buffer.

In a specific embodiment, the vaginal care composition comprises, by weight of the total composition:
(a) 10% exosomes (e.g., stem cell-derived exosomes such as MSC-derived exosomes),
(b) 25% antioxidant, and
(c) 60-65% (60%, 61%, 62%, 63%, 64%, or 65%) pH buffer.

In a specific embodiment, the vaginal care composition comprises, by weight of the total composition:
(a) 1% exosomes (e.g., stem cell-derived exosomes such as MSC-derived exosomes),
(b) 20% antioxidant, and
(c) 60-79% (60%, 61%, 62%, 63%, 64%, 65%, 66%, 67%, 68%, 69%, 70%, 71%, 72%, 73%, 74%, 75%, 76%, 77%, 78%, or 79%) pH buffer.

In a specific embodiment, the vaginal care composition comprises, by weight of the total composition:
(a) 0.5% exosomes (e.g., stem cell-derived exosomes such as MSC-derived exosomes),
(b) 20% antioxidant, and
(c) 60-79.5% (60%, 61%, 62%, 63%, 64%, 65%, 66%, 67%, 68%, 69%, 70%, 71%, 72%, 73%, 74%, 75%, 76%, 77%, 78%, 79%, or 79.5%) pH buffer.

In a specific embodiment, the vaginal care composition comprises, by weight of the total composition:
(a) 0.3% exosomes (e.g., stem cell-derived exosomes such as MSC-derived exosomes),
(b) 20% antioxidant, and
(c) 60-79.7% (60%, 61%, 62%, 63%, 64%, 65%, 66%, 67%, 68%, 69%, 70%, 71%, 72%, 73%, 74%, 75%, 76%, 77%, 78%, 79%, or 79.7%) pH buffer.

In a specific embodiment, the vaginal care composition comprises, by weight of the total composition:
(a) 0.1% exosomes (e.g., stem cell-derived exosomes such as MSC-derived exosomes),
(b) 20% antioxidant, and
(c) 60-79.9% (60%, 61%, 62%, 63%, 64%, 65%, 66%, 67%, 68%, 69%, 70%, 71%, 72%, 73%, 74%, 75%, 76%, 77%, 78%, 79%, or 79.9%) pH buffer.

In some embodiments, the vaginal care composition further comprises a pharmaceutically acceptable carrier. In some embodiments, the vaginal care composition further comprises a lyoprotectant.

In some embodiments, the exosomes are lyophilized and mixed with the antioxidant and the pH buffer as a powder.

In some embodiments, the exosomes comprise mesenchymal stem cell (MSC)-derived exosomes, bone marrow-derived exosomes, stem cell-derived exosomes, cord blood-derived exosomes, hepatocyte-derived exosomes, lung-derived exosomes, neutrophil-derived exosomes, or plasma-derived exosomes.

In a specific embodiment, the exosomes comprise MSC-derived exosomes. MSCs were shown to be present in essentially all adult mammalian organs and tissues. In some embodiments, MSCs from which exosomes are derived are isolated from tissues selected from adipose tissue, articular cartilage, brain, dental tissues, endometrium and menstrual blood or skin. In some embodiments, MSCs are derived from perinatal organs and tissues that are generally discarded after delivery, such as amniotic fluid, amniotic membrane, placenta, Wharton's jelly, umbilical cord tissue and cord blood. MSCs suitable for use according to the instant application include the MSCs described in Kozlowska et al., (World journal of stem cells, 11.6 (2019): 347), which is incorporated herein by reference in its entirety.

In some embodiments, the pH of the composition is between pH 4.5 and pH 6.5 or between pH 3.5 and pH 7 (e.g., pH 3.5, pH 4, pH 4.5, pH 5, pH 5.5, pH 6. pH 6.5, or pH 7).

In some embodiments, the composition comprises between 5%-40%, between 10%-30%, or between 15%-25% MSC-derived exosomes.

In some embodiments, the composition comprises between 10%-15%, between 15%-20%, or between 10%-20% antioxidant.

In some embodiments, the composition comprises between 30%-40%, between 25%-45%, or between 25%-35% pH buffer.

In some embodiments, the antioxidant is selected from L-carnosine, D-carnosine, acetyl-carnosine, anserine, alanine, L-histidine, D-histidine, or a combination thereof. In some embodiments, the antioxidant prevents protein aggregation in the composition. In some embodiments, the antioxidant has vasodilative properties.

In a specific embodiment, the antioxidant is L-carnosine. In some embodiments, L-carnosine prevents protein aggregation in the composition. In some embodiments, L-carnosine has vasodilative properties.

In some embodiments, the pH buffer is selected from magnesium citrate, magnesium sulfate, sodium citrate, sodium sulfate, salts of magnesium, sodium, zinc or potassium, or a combination thereof. In some embodiments, the pH buffer is present in the vagina care composition in solid form (e.g., powder). In some embodiments, the pH buffer also acts as a preservative for the composition.

In a specific embodiment, the pH buffer is magnesium citrate. In some embodiments, the magnesium citrate also acts as a preservative for the composition.

In some embodiments, the vaginal care composition further comprises at least one of the following constituents: a *Lactobacillus* strain, *Saccharomyces cerevisiae*, vitamin A, D-alpha-tocopherol, pantothenate, zinc, selenium, or oligofructose.

In some embodiments, the *Lactobacillus* strain is selected from *Lactobacillus bifidus*, *Lactobacillus rhamnosus*, *Lactobacillus acidophilus*, *Lactobacillus crispatus*, *Lactobacillus fermentum*, *Lactobacillus plantarum*, *Lactobacillus casei*, *Lactobacillus paracasei*, *Lactobacillus jensenii*, *Lactobacillus gasseri*, *Lactobacillus cellobiosis*, *Lactobacillus brevis*, *Lactobacillus delbrueckii*, *Lactobacillus rogosae*, or *Lactobacillus bifidum*.

In some embodiments, the *Lactobacillus* strain in the composition is viable. In a specific embodiment, the *Lactobacillus* strain is viable *Lactobacillus bifidus*. In some embodiments, the *Saccharomyces cerevisiae* is not viable.

In some embodiments, the zinc in the composition is in the form of zinc sulfate and/or zinc gluconate.

In some embodiments, the vitamin A in the composition is in the form of retinyl acetate and/or retinyl gluconate.

In some embodiments, the vaginal care composition further comprises at least one of the following constituents: sunflower oil, Tegomuls 90 S, cetyl alcohol, cetaceum artificiale (cetyl palmitate), Polysorbate 80, methyl 4-hydroxybenzoate, propyl 4-hydroxybenzoate, sesame oil, wool wax, yellow wax, wool wax alcohols, glycerol, glycerol ester, palmitic acid ester, vaseline, cocoa butter, liquid wax, olive oil, or distilled water.

In some embodiments, the vaginal care composition further comprises at least one of the following constituents: an antibiotic agent, a free radical generating agent, an antifungal agent, an antiviral agent, a nucleoside-analog reverse transcriptase inhibitor, a non-nucleoside reverse transcriptase inhibitor, a protease inhibitor, an immunosuppressant, an anti-inflammatory agent, a retinoid agent, a tar agent, an antihistamine agent, or an antipruritic agent.

In some embodiments, (a) the antibiotic agent is selected from chloramphenicol, tetracyclines, synthetic and semi-synthesic penicillins, beta-lactames, quinolones, fluoroquinolnes, macrolide antibiotics, peptide antibiotics, cyclosporines, erytromycin and clinndamycin; (b) the free radical generating agent is benzoyl peroxide; (c) the antifungal agent is selected from azoles, diazole, triazole, miconazole, fluconazole, ketoconazole, clotrimazole, itraconazole griseofulvin, ciclopirox, amorolfine, terbinafine, Amphotericin B and potassium iodide; (d) the antiviral agent is selected from the group of flucytosine (5FC), Vidarabine, acyclovir and Gancyclovir; (e) the nucleoside-analog reverse transcriptase inhibitor is selected from Zidovudine, Stavudine and Lamivudine; (f) the non-nucleoside reverse transcriptase inhibitor is selected from Nevirapine and Delavirdine; (g) the protease inhibitor is selected from Saquinavir, Ritonavir, Indinavir, Nelfinavir, Ribavirin Amantadine, Rimantadine and Interferon; (h) the immunosuppressant is selected from Clobetasol proprionate, Halobetasol proprionate, Betamethasone diproprionate, Betamethasone valerate, Fluocinolone acetonide, Halcinonide, Betamethasone valerate, Fluocinolone acetonide, Hydrocortisone valerate, Triamcinolone acetonide, Hydrocortisone and hexachlorobenzene; (i) the anti-inflammatory agent is selected from a vitamin B3 derivative, a corticosteroid (e.g., hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amc, amcinafide, betamethasone and the balance of its esters, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and mixtures thereof), and a nonsteroidal anti-inflammatory drug (e.g., propionic acid derivatives; acetic acid derivatives; fenamic acid derivatives; biphenylcarboxylic acid derivatives; and oxicams, all of which are fully described in the U.S. Pat. No. 4,985,459 incorporated herein in its entirety); (j) the retinoid agent is selected from isotretinoin, adapalene and tretinoin; (k) the tar agent is selected from coal tar and cade oil; and (1) the antihistamine agent is doxepine hydrochloride; and/or (m) the antipruritic agent is crotampiton.

In some embodiments, the composition is a capsule, an ovule, a cream, an ointment or a tampon.

Methods for Improving Vaginal Health

Another aspect of the disclosure is directed to a method for improving vaginal health in a subject, comprising administering to the subject in need thereof a vaginal care composition of the instant disclosure comprising stem cell-derived exosomes (e.g., mesenchymal stem cell (MSC)-derived exosomes), an antioxidant, and a pH buffer.

The vaginal health of the subject is improved after administration of the vaginal care composition of the instant disclosure as compared to before the administration with regards to at least one of the following vaginal conditions: vaginal dryness, irritation, dyspareunia, decreased lubrication, decreased arousal, post-coital bleeding, infections, vaginal or pelvic pain. In some embodiments, improvement in vaginal health is observed within 1 day, 2 days, 3, days, 1 week, 2 weeks, 3 weeks, 1 month, 6 weeks, or 2 months of the first administration of the vaginal care composition.

In some embodiments, the subject is suffering from genitourinary syndrome of menopause (GSM). In some embodiments, the subject is suffering from bacterial vaginosis, stress urinary incontinence (SUI) or urinary tract infection (UTI). In some embodiments, administration of the vaginal care composition improves the symptoms of GSM with regards to at least one of the following vaginal conditions: vaginal dryness, irritation, dyspareunia, decreased lubrication, decreased arousal, post-coital bleeding, infections, vaginal or pelvic pain.

In some embodiments, the subject suffers from high vaginal pH. In some embodiments, the subject's vaginal pH is over pH 5 (e.g., pH 5.1, pH 5.5, pH 6, pH 6.5, pH 7 or higher). In some embodiments, administration of the vaginal care composition results in restoration of the vaginal pH to normal levels, i.e., between pH 3.8 and pH 4.5 (e.g., pH 3.8, pH 3.9, pH 4, pH 4.1, pH 4.2, pH 4.3, pH 4.4 or pH 4.5). In some embodiments, increase in vaginal pH is observed within 1 day, 2 days, 3, days, 1 week, 2 weeks, 3 weeks, 1 month, 6 weeks or 2 months of the first administration of the vaginal care composition.

In some embodiments, the vaginal care composition comprises, by weight of the total composition:
(a) 1%-50% (e.g., 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%) exosomes (e.g., stem cell-derived exosomes such as MSC-derived exosomes),
(b) 10%-25% (e.g., 10%, 11%, 12%, 13%, 14%, 15%, 16%, 17%, 18%, 19%, 20%, 21%, 22%, 23%, 24%, or 25%) antioxidant, and
(c) a pH buffer.

In some embodiments, the vaginal care composition comprises, by weight of the total composition:
(a) 1%-50% (e.g., 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%) exosomes (e.g., stem cell-derived exosomes such as MSC-derived exosomes),
(b) 10%-25% (e.g., 10%, 11%, 12%, 13%, 14%, 15%, 16%, 17%, 18%, 19%, 20%, 21%, 22%, 23%, 24%, or 25%) antioxidant, and
(c) 25%-50% (e.g., 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%) pH buffer.

In some embodiments, the vaginal care composition comprises, by weight of the total composition:
(a) 1%-40% (e.g., 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40%) exosomes (e.g., stem cell-derived exosomes such as MSC-derived exosomes), (b) 10%-20% (e.g., 10%, 11%, 12%, 13%, 14%, 15%, 16%, 17%, 18%, 19%, or 20%) antioxidant, and (c) 25%-75% (e.g., 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%) pH buffer.

In some embodiments, the vaginal care composition comprises, by weight of the total composition:

(a) 1%-30% (e.g., 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, 25%, 26%, 27%, 28%, 29%, or 30%) exosomes (e.g., stem cell-derived exosomes such as MSC-derived exosomes), (b) 10%-25% (e.g., 10%, 11%, 12%, 13%, 14%, 15%, 16%, 17%, 18%, 19%, 20%, 21%, 22%, 23%, 24%, or 25%) antioxidant, and (c) 35%-75% (e.g., 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%) pH buffer.

In some embodiments, the vaginal care composition comprises, by weight of the total composition:

(a) 1%-10% (e.g., 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%) exosomes (e.g., stem cell-derived exosomes such as MSC-derived exosomes), (b) 15%-25% (e.g., 15%, 16%, 17%, 18%, 19%, 20%, 21%, 22%, 23%, 24% or 25%) antioxidant, and (c) 55%-75% (e.g., 55%, 56%, 57%, 58%, 59%, 60%, 61%, 62%, 63%, 64%, 65%, 66%, 67%, 68%, 69%, 70%, 71%, 72%, 73%, 74%, or 75%) pH buffer.

In some embodiments, the vaginal care composition comprises, by weight of the total composition:

(a) 5%-10% (e.g., 5%, 5.5%, 6%, 6.5%, 7%, 7.5%, 8%, 8.5%, 9%, 9.5%, or 10%) exosomes (e.g., stem cell-derived exosomes such as MSC-derived exosomes), (b) 15%-20% (e.g., 15%, 16%, 17%, 18%, 19%, or 20%) antioxidant, and (c) 25%-75% (e.g., 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%) pH buffer.

In a specific embodiment, the vaginal care composition comprises, by weight of the total composition:

(a) 5% exosomes (e.g., stem cell-derived exosomes such as MSC-derived exosomes), (b) 20% antioxidant, and (c) 60-75% (60%, 61%, 62%, 63%, 64%, 65%, 66%, 67%, 68%, 69%, 70%, 71%, 72%, 73%, 74%, or 75%) pH buffer.

In a specific embodiment, the vaginal care composition comprises, by weight of the total composition:

(a) 10% exosomes (e.g., stem cell-derived exosomes such as MSC-derived exosomes), (b) 25% antioxidant, and (c) 60-65% (60%, 61%, 62%, 63%, 64%, or 65%) pH buffer.

In some embodiments, the vaginal care composition further comprises a pharmaceutically acceptable carrier.

In some embodiments, the exosomes are lyophilized and mixed with the antioxidant and the pH buffer as a powder.

In some embodiments, the exosomes comprise mesenchymal stem cell (MSC)-derived exosomes, bone marrow-derived exosomes, stem cell-derived exosomes, cord blood-derived exosomes, hepatocyte-derived exosomes, lung-derived exosomes, neutrophil-derived exosomes, or plasma-derived exosomes. In a specific embodiment, the exosomes comprise MSC-derived exosomes.

In some embodiments, the pH of the composition is between pH 4.5 and pH 6.5 or between pH 3.5 and pH 7 (e.g., pH 3.5, pH 4, pH 4.5, pH 5, pH 5.5, pH 6, pH 6.5, or pH 7).

In some embodiments, the composition comprises between 5%-40%, between 10%-30%, or between 15%-25% MSC-derived exosomes.

In some embodiments, the composition comprises between 10%-15%, between 15%-20%, or between 10%-20% antioxidant.

In some embodiments, the composition comprises between 30%-40%, between 25%-45%, or between 25%-35% pH buffer.

In some embodiments, the antioxidant is selected from L-carnosine, D-carnosine, acetyl-carnosine, anserine, alanine, L-histidine, D-histidine, or a combination thereof. In some embodiments, the antioxidant prevents protein aggregation in the composition. In some embodiments, the antioxidant has vasodilative properties.

In a specific embodiment, the antioxidant is L-carnosine. In some embodiments, L-carnosine prevents protein aggregation in the composition. In some embodiments, L-carnosine has vasodilative properties.

In some embodiments, the pH buffer is selected from magnesium citrate, magnesium sulfate, sodium citrate, sodium sulfate, salts of magnesium, sodium, zinc or potassium, or a combination thereof. In some embodiments, the pH buffer is present in the vagina care composition in solid form (e.g., powder). In some embodiments, the pH buffer also acts as a preservative for the composition.

In a specific embodiment, the pH buffer is magnesium citrate. In some embodiments, the magnesium citrate also acts as a preservative for the composition.

In some embodiments, the vaginal care composition further comprises at least one of the following constituents: a *Lactobacillus* strain, *Saccharomyces cerevisiae*, vitamin A, D-alpha-tocopherol, pantothenate, zinc, selenium, or oligofructose.

In some embodiments, the *Lactobacillus* strain is selected from *Lactobacillus bifidus, Lactobacillus rhamnosus, Lactobacillus acidophilus, Lactobacillus crispatus, Lactobacillus fermentum, Lactobacillus plantarum, Lactobacillus casei, Lactobacillus paracasei, Lactobacillus jensenii, Lactobacillus gasseri, Lactobacillus cellobiosis, Lactobacillus brevis, Lactobacillus delbrueckii, Lactobacillus rogosae*, and *Lactobacillus bifidum*.

In some embodiments, the *Lactobacillus* strain in the composition is viable. In some embodiments, the *Saccharomyces cerevisiae* is not viable.

In some embodiments, the zinc in the composition is in the form of zinc sulfate and/or zinc gluconate.

In some embodiments, the vitamin A in the composition is in the form of retinyl acetate and/or retinyl gluconate.

In some embodiments, the vaginal care composition further comprises at least one of the following constituents: sunflower oil, Tegomuls 90 S, cetyl alcohol, cetaceum artificiale (cetyl palmitate), Polysorbate 80, methyl 4-hydroxybenzoate, propyl 4-hydroxybenzoate, sesame oil, wool wax, yellow wax, wool wax alcohols, glycerol, glycerol ester, palmitic acid ester, vaseline, cocoa butter, liquid wax, olive oil or distilled water.

In some embodiments, the vaginal care composition further comprises at least one of the following constituents: an antibiotic agent, a free radical generating agent, an antifungal agent, an antiviral agent, a nucleoside-analog reverse transcriptase inhibitor, a non-nucleoside reverse transcriptase inhibitor, a protease inhibitor, an immunosuppressant, an anti-inflammatory agent, a retinoid agent, a tar agent, an antihistamine agent, and an antipruritic agent.

In some embodiments, (a) the antibiotic agent is selected from chloramphenicol, tetracyclines, synthetic and semi-synthesic penicillins, beta-lactames, quinolones, fluoroquinolnes, macrolide antibiotics, peptide antibiotics, cyclosporines, erytromycin and clinndamycin; (b) the free radical generating agent is benzoyl peroxide; (c) the antifungal agent is selected from azoles, diazole, triazole, miconazole, fluconazole, ketoconazole, clotrimazole, itraconazole griseofulvin, ciclopirox, amorolfine, terbinafine, Amphotericin B and potassium iodide; (d) the antiviral agent is selected from the group of flucytosine (5FC), Vidarabine, acyclovir and Gancyclovir; (e) the nucleoside-analog reverse transcriptase inhibitor is selected from Zidovudine, Stavudine and Lamivudine; (f) the non-nucleoside reverse transcriptase inhibitor is selected from Nevirapine and Delavirdine; (g) the protease inhibitor is selected from Saquinavir, Ritonavir, Indinavir, Nelfinavir, Ribavirin Amantadine, Rimantadine and Interferon; (h) the immunosuppressant is selected from Clobetasol proprionate, Halobetasol proprionate, Betamethasone diproprionate, Betamethasone valerate, Fluocinolone acetonide, Halcinonide, Betamethasone valerate, Fluocinolone acetonide, Hydrocortisone valerate, Triamcinolone acetonide, Hydrocortisone and hexachlorobenzene; (i) the anti-inflammatory agent is selected from a vitamin B3 derivative, a corticosteroid (e.g., hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amc, amcinafide, betamethasone and the balance of its esters, chlorprednisone, chlorprednisone acetate, clocortelone, clescinolone, dichlorisone, difluprednate, flucloronide, flunisolide, fluorometholone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and mixtures thereof), and a non-steroidal anti-inflammatory drug (e.g., propionic acid derivatives; acetic acid derivatives; fenamic acid derivatives; biphenylcarboxylic acid derivatives; and oxicams, all of which are fully described in the U.S. Pat. No. 4,985,459 incorporated herein in its entirety); (j) the retinoid agent is selected from isotretinoin, adapalene and tretinoin; (k) the tar agent is selected from coal tar and cade oil; and (l) the antihistamine agent is doxepine hydrochloride; and/or (m) the antipruritic agent is crotampiton.

In some embodiments, the composition is a capsule, an ovule, a cream, an ointment or a tampon. In some embodiments, the composition is administered intra-vaginally.

In some embodiments, the composition is a capsule for intra-vaginal administration, wherein the capsule comprises 5-100 mg (e.g., 5, 10, 15, 20, 25, 30, 35, 40, 45, 50, 55, 60, 65, 75, 80, 85, 90, 95, or 100 mg) of MSC-derived exosomes (per 100 mg of total capsule weight). In some embodiments, the composition further comprises L-carnosine and magnesium citrate, in addition to MSC-derived exosomes.

In some embodiments, the vaginal care composition is a capsule for intra-vaginal administration, wherein the capsule comprises per 100 mg, 3-20 (e.g., 3, 4, 5, 6, 7, 8, 9, 10, 11, 12, 13, 14, 15, 16, 17, 18, 19 or 20) mg MSC-derived exosomes, 10-20 (e.g., 10, 11, 12, 13, 14, 16, 17, 18, 19 or 20) mg L-carnosine, and 50-75 (e.g., 50, 51, 52, 53, 54, 55, 56, 57, 58, 59, 61, 62, 63, 64, 65, 66, 67, 68, 69, 70, 71, 72, 73, 74 or 75) mg magnesium citrate, optionally wherein the MSC-derived exosomes in the composition are lyophilized.

In some embodiments, the vaginal care composition is a capsule for intra-vaginal administration, wherein the capsule comprises per 100 mg, 5 mg MSC-derived exosomes, 20 mg L-carnosine and 70-75 mg magnesium citrate, optionally wherein the MSC-derived exosomes in the composition are lyophilized.

In some embodiments, the vaginal care composition is a capsule for intra-vaginal administration, wherein the capsule comprises per 100 mg, 10 mg MSC-derived exosomes, 20 mg L-carnosine and 65-70 mg magnesium citrate, optionally wherein the MSC-derived exosomes in the composition are lyophilized.

In some embodiments, the composition is administered using a panty liner. In some embodiments, the panty liner contains the vaginal care composition on an upper layer. In some embodiments, the panty liner is designed in such a manner that the vaginal care composition is contained solely in a layer directly beneath the cover layer of the panty liner. The vaginal care composition can be applied to/introduced onto any panty liner by methods known to the person skilled in the art. In some embodiments, the panty liner may consist of a moisture-permeable cover layer, a moisture-repelling layer arranged beneath it, a moisture-storing layer arranged beneath the moisture-repelling layer, and a backing layer that is impermeable to liquid. In some embodiments, the cover layer has pores, for example, which facilitate the drawing off of liquid and improve aeration. In some embodiments, masking substances which improve the appearance of the panty liner may also be present.

In some embodiments, the composition is administered once every hour, every two hours, every three hours, every six hours, every 12 hours, every 16 hours, every day, every two days, every three days, every four days, every five days, every six days, every week, every two weeks, or every four weeks.

In some embodiments, the composition is administered intra-vaginally every hour, every two hours, every three hours, every six hours, every twelve hours, every day, every two days, every three days, every five days, every seven days, every ten days, or every fourteen days. In some embodiments, the vaginal care composition is a capsule for intra-vaginal administration; wherein the capsule comprises 5-100 mg MSC-derived exosomes, L-carnosine, and magnesium citrate; and wherein the subject receives one capsule every week. In some embodiments, the vaginal care composition is a capsule for intra-vaginal administration;

wherein the capsule comprises 5-100 mg MSC-derived exosomes, L-carnosine, and magnesium citrate; and wherein the subject receives two capsules every week. In some embodiments, the vaginal care composition is a capsule for intra-vaginal administration; wherein the capsule comprises 5-100 mg MSC-derived exosomes, L-carnosine, and magnesium citrate; and wherein the subject receives three capsules every week.

In some embodiments, the subject has been suffering from at least one of the following: vaginal dryness, irritation, dyspareunia, reduced lubrication, post-coital bleeding, decreased arousal, infections, vaginal or pelvic pain. In some embodiments where the subject suffers from a vaginal pH of 5.5 or more, or 6.0 or more, or 6.5 or more, the vaginal care composition reduces the vaginal pH of the subject by at least 0.5, or at least 1.0, or at least 1.5 after 30 days of treatment. In some embodiments where the subject suffers from a vaginal pH of 5.5 or more, or 6.0 or more, or 6.5 or more, the vaginal care composition reduces the vaginal pH of the subject by at least 0.5, or at least 1.0, or at least 1.5, or at least 2.0 after 60 days of treatment.

Exosomes

As used herein the term "exosome" refers to cell-derived vesicles with a diameter of, for example, between about 30 to about 150 nm, which diameter is larger than LDL, but much smaller than, for example, red blood cells. Exosomes may be released from a cell when multivesicular bodies fuse with the plasma membrane or they may be released directly from the plasma membrane.

In some embodiments, the exosomes comprise mesenchymal stem cell (MSC)-derived exosomes, bone marrow-derived exosomes, stem cell-derived exosomes, cord blood-derived exosomes, hepatocyte-derived exosomes, lung-derived exosomes, neutrophil-derived exosomes, or plasma-derived exosomes. In a specific embodiment, the exosomes comprise MSC-derived exosomes.

In some embodiments, the exosomes used in the compositions and methods of this disclosure are prepared from conditioned media from mesenchymal stem cells ("MSC-derived exosomes"). After conditioned media is isolated, exosomes may be extracted from media by methods known in the art. See, e.g., Taylor et al., Methods in Mol. Biol. 728:235-246, 2011, which is incorporated herein by reference in its entirety.

In some embodiments, the conditioned media is centrifuged at 12,000×g for about 15 minutes at about 4° C. (low speed centrifugation). The resulting supernatant may then be centrifuged at 100,000×g for about 1 hour at about 4° C. The resulting pellet may then be re-suspended in 4° C. phosphate buffered saline (i.e., PBS; other physiological buffers may be used), and the re-suspended material may then be re-centrifuged for 1 hour at 100,000×g, 4° C., and resuspended in PBS until use.

In some embodiments, the exosomes may be isolated by column chromatography. As stated above, the conditioned media may be centrifuged at 12,000×g for about 15 minutes at about 4° C. After low speed centrifugation, an aliquot of the supernatant (e.g., 2-3 ml) is applied to a 2% agarose based gel column (2.5×16 cm). For optimum separation, the sample volume can be about 1/20 of the total column volume (as defined by πr2h). The material may then be eluted isocratically with PBS at a flow rate of about 1 ml/min, monitoring the eluate at 280 nm, where fractions are collected (2-3 ml). The void volume fractions are pooled, and centrifuged at 100,000×g for 1 hour at 4° C., where the pelleted exosomes may be recentrifuged after suspension in PBS, and finally resuspended in PBS until use.

Alternatively, populations of exosomes may be enriched by absorption to antibody conjugated magnetic microbeads. For example, anti-surface-antigen Ab-magnetic beads (about 50 µl) may be mixed with about 2 ml of low speed centrifugation conditioned media supernatant, and incubated on a shaker at room temperature. After a sufficient time (about 2 hours), tubes containing the immune complexes are placed in a magnetic separator, the fluid is removed, leaving the magnetic beads and bound exosomes attached to the side of the tubes. The tubes may then be removed from the magnetic separator, where the beads are rinsed with about 500 µl of Tris buffered saline (although other buffers may be used) and the separation repeated. The isolated exosomes/ microbeads may be diluted in IgG elution buffer (Pierce Chemical Co, Rockford, IL) and the complex centrifuged at about 10,000 rpm (low speed centrifuge) to separate the microbeads from the exosomes (supernatant). The supernatant may then be centrifuged at 100,000×g for about 1 hour at 4° C. The pelleted exosomes may then be resuspended in about 250 µl phosphate-buffered saline (PBS).

Other methods include the use of EXOQUICK™ (available from System Biosciences Inc, Mountain View, CA; see Taylor et al. (2011), supra) polymer-based precipitation methods. Typical exosome yields from cell culture may be from about 0.5 to about 0.7 µg/ml culture, about 0.7 to about 1.0 µg/ml culture, about 1.0 to about 2.0 µg/ml culture, about 2.0 to about 4.0 µg/ml culture, or about 4.0 to about 10.0 µg/ml culture.

Once isolated, the exosomes may be analyzed for protein/ RNA analysis or may be used to form vaginal care compositions such as capsules, creams, lotions, serums, ointments, tampons or hydrogels. The vaginal care compositions of the instant disclosure can be delivered as capsules, creams, lotions, serums, ointments, tampons or hydrogels.

In some embodiments, the exosomes used in the compositions of the instant disclosure are lyophilized. In some embodiments, the exosomes are lyophilized in 1%-10% of a stabilizing agent (e.g., 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%) by volume. In some embodiments, the stabilizing agent is selected from sucrose, mannitol or trehalose.

EXAMPLES

Example 1—Exosome Production

An exemplary process for producing MSC-derived exosomes is shown in FIG. 1. Briefly, MSCs (CD45−/CD105+) were isolated from human tissue. MSCs were cultured and expanded in tissue culture flasks. Supernatant was harvested and saved for further exosome characterization. Cells were harvested and frozen. Prior to freezing, a sample of the cell harvest was taken and saved for further characterization (e.g., to confirm correct MSC surface markers including CD45−/CD105+). Both cells and supernatant were tested for safety. Production of exosomes was achieved by expanding MSCs. Supernatant was harvested and characterized for process controls. At the end of production, cells were harvested and a sample taken for further characterization to confirmed (CD45−/CD105+) and safety tests. Harvested supernatant underwent further purification process by column chromatography and ultrafiltration techniques. Final product was sterile filtered.

Example 2—Manufacturing of Capsules

Lyophilization process: Measure amount of desired exosome solution. Add 1%-10% (e.g., 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%) by volume of a stabilizing agent selected from sucrose, mannitol or trehalose.

Carnosine functions as a biological pH buffer and antioxidant. Carnosine has protein stability benefits and prevents aggregation along with vasodilation benefits. Magnesium citrate is a magnesium salt used to regulate pH along with preservation.

Manufacturing Process for 1000 capsules each at 100 mg containing 5 mg exosome, 20 mg L-carnosine, and 75 mg magnesium citrate.

Materials: exosomes 5 grams, L-carnosine 20 grams, magnesium citrate 75 grams.

Steps for manufacturing: (1) calibrate scale; (2) accurately weigh out each of the materials using lab scoop; (3) sieve each material into one weighing dish; (4) add material to V-Blender; (5) turn on V-Blender and blend for 60 minutes; (6) empty material from V-Blender into clean weighing dish; (7) fill capsules with blended material.

Example 3—Vaginal Care Composition Restores Vaginal pH to Normal Levels in GSM Patients Normally, vaginal pH is about 3.8 to 4.5. However, during genitourinary syndrome of menopause (GSM), and other vaginal disorders vaginal pH increases (i.e., vagina becomes less acidic/more alkaline). In turn, high pH negatively affects vaginal health and vaginal flora.

Figure 2:
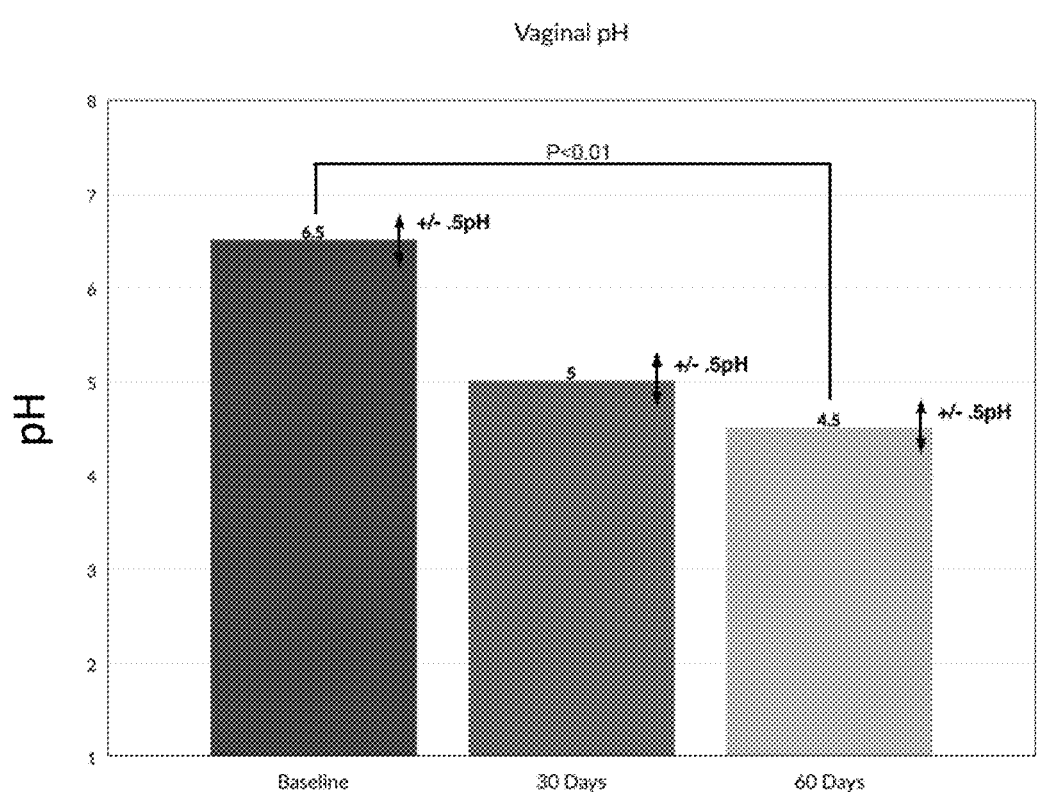
FIG. 2. Bar graph showing vaginal pH measurements from subjects suffering from genitourinary syndrome of menopause (GSM). Prior to administration (baseline) of the vaginal care composition of the instant disclosure, the subjects had vaginal acidity of about pH 6.5. The subjects received a dosing of one capsule per week for the first 60 days. The capsule was administered by using a finger and/or an applicator, then gently pushing and inserting as far as it will comfortably go up into the vaginal cavity. The subjects laid down immediately after the intra-vaginal administration. The vaginal pH of the subjects decreased to about pH 5 at day 30, and to about pH 4.5 at day 60 after intra-vaginal administration of the vaginal care composition. Average n=6.

FIG. 2 shows vaginal pH measurements taken from post-menopausal subjects suffering from genitourinary syndrome of menopause (GSM) before and after (30 and 60 days after) administration of the vaginal care composition. None of the subjects were on any type of hormone replacement therapy before the treatment.

In this example, the vaginal care composition was an intra-vaginal capsule comprising 5 mg lyophilized MSC-derived exosomes, 20 mg L-carnosine and 70-75 mg magnesium citrate.

The vaginal care composition used in this example was produced as follows: production of the formulation started with lyophilized exosomes which were measured with L-carnosine and magnesium citrate, and put into a V-blender to form a homogeneous mixture of free-flowing powder. Once the mixture was completed, the powdered composition was put into capsules and packaged.

Prior to administration of the vaginal care composition of the instant disclosure (baseline), the vaginal pH was measured to be about pH 6.5. The subjects received a dosing of one capsule per week for the first 60 days. The capsule was administered by using a finger, then gently pushing and inserting as far as it will comfortably go up into the vaginal cavity. The subjects laid down immediately after the intra-vaginal administration. The vaginal pH of the subjects decreased to about pH 5 at day 30, and to about pH 4.5 at day 60, after start of the treatment with the vaginal care composition (FIG. 2). Therefore, the vaginal care composition of the instant disclosure can restore vaginal pH levels of GSM patients to normal levels.

In addition to vaginal pH, the patient also reported improved vaginal moisture and sensitivity, which shows promising effects in treating atrophy.

Example 4—Vaginal Care Composition Increases cAMP in Vaginal Cells

Methods: About $1.4 \times 10^4$ primary human vaginal epithelial cells were seeded in complete growth medium (ATCC) overnight at 37° C., 5% $CO_2$, and then transferred to Induction Buffer (Promega). Cells were either exposed to exosomes for 60 minutes or to forskolin for 30 minutes. As used herein, "rate per cell" refers to the number of exosomes per cell. A rate per cell of 7 means, on average, 7 exosomes were administered per cell in the culture. For instance, for a stock exosome concentration of $200 \times 10^6$ exosomes per mL, 10 ul of the stock (or $2 \times 10^6$ exosomes) comes to about 142 exosomes per cell.

The cyclic AMP (cAMP) was evaluated using cAMP-Glo Assay (Promega). The cAMP-Glo™ Assay is designed to monitor cAMP production in response to the effects of test compounds. This assay is based on the principle that cAMP stimulates protein kinase A holoenzyme activity, decreasing available ATP and leading to a diminished luminescence emission.

Results: Human vaginal cells that were exposed to exosomes in the vaginal care composition for 60 minutes showed a significant increase in cAMP production. It is believed that the higher concentrations of exosomes promoted the cAMP production so much as to reset the cAMP levels by compensatory mechanisms. Similarly, a 60-minute treatment with forskolin (positive control) also showed less cAMP production due to regeneration of cAMP.

Without being bound to a particular theory, the vaginal care composition comprising mesenchymal-derived exosomes provide the observed effect, at least in part, by promoting vaginal remodeling by acting on extracellular matrix (ECM). Exosomes are believed to modulate the matrix metalloproteinases and tissue inhibitor of matrix metalloproteinases-1 affecting collagen production. When exosomes are applied to a localized area intra-vaginally, there is a marked increase in transudate causing increased lubrication along with increased firmness. Exosomes regulate the cytokines transforming growth factor beta 3 and beta 1 (TGF). Transforming growth factor is a cytokine that induces angiogenesis contributing to vaginal firmness. Additionally, the regulation of vaginal pH was noted, especially in menopausal women. The proposed mechanism of pH regulation comes from the exosomes causing an increase in intracellular cyclic adenosine monophosphate (cAMP) and cyclic guanosine monophosphate (cGMP) which increases glycolytic flux and lactic acid production.

Example 5: Vaginal Care Composition Decreases Vaginal Dryness and Pain 10 women were surveyed using The Yale Visual Analogue Scale before and after using the vaginal care composition. The women rated their experience on dryness and pain from 0-10 (0 being no dryness/no pain; 10 being most dry/most painful).

The following inclusion and exclusion criteria were used in selecting the subjects: Perimenopausal and menopausal women, women showing symptoms of vulvovaginal dryness, women showing symptoms of painful sex due to dryness or atrophy, women with no treatments of symptoms for the past year, women with no use of estrogen based devices, and women with no use of vaginal Hyaluronic acid (HA), collagen, platelet-rich plasma (prp), carboxytherapy in the past year were included in the study. In contrast, women who received treatments for vaginal dryness or pain symptoms for past year, women who used estrogens locally, women who used vaginal HA, collagen, prp, or carboxytherapy in the past year were excluded from the study.

The subjects intra-vaginally applied intra-vaginal capsules comprising 5 mg exosomes, mg L-carnosine, and 75 mg magnesium citrate twice a week for 60 days.

Results: Women included in the study reported a significant decrease in vaginal dryness (FIG. 3A) and vaginal pain (FIG. 3B) when they used the vaginal care composition for 60 days.

Example 6: Vaginal Care Composition Increases Collagen Production in Vaginal Cells Methods: Between $1 \times 10^4$ and $1 \times 10^8$ human vaginal epithelial cells are seeded in complete growth medium (ATCC) overnight at 37° C., 5% $CO_2$, and then transferred to Induction Buffer (Promega). Cells are either exposed to exosomes for 10, 30 or 60 minutes (between 3-200 rate per cell, e.g., 3, 7, 28, 142 or 200 rate per cell/exosomes per cell) or to forskolin (positive control) for 30 minutes (at 1, 10 or 100 µM).

Briefly, cells are resuspended in 2.5% acetic acid containing 0.1 mg/mL pepsin. Cells are disrupted on ice. The homogenate is sonicated on ice with a probe sonicator, and centrifuged at 12,000 g for 10 minutes. Supernatant is recovered and transferred to a new tube. Protein concentration is determined by a protein assay. The pH of the sample is neutralized by first adding 2N sodium hydroxide solution 1:6 directly on the sample. Then, 10×PBS is added 1:10 directly to the sample to the final concentration of 1×PBS. The sample is then used for collagen detection. Collagen detection assay is performed with Abcam's Soluble Collagen Assay Kit (ab242291) according to the manufacturer's instructions.

Results: Exosome-treated vaginal cells have increased collagen production. Exosomes are believed to modulate the matrix metalloproteinases and tissue inhibitor of matrix metalloproteinases-1 to cause an increase in collagen production.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

The terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entireties, including all figures and tables, to the extent they are not inconsistent with the explicit teachings of this specification.

What is claimed is:

1. A vaginal care composition comprising, by weight of the total composition: (a) 1%-50% mesenchymal stem cell (MSC)-derived exosomes, (b) 10%-25% L-carnosine, and (c) 25%-75% magnesium citrate, wherein the composition is a capsule for intra-vaginal administration, wherein the capsule comprises 5-100 mg of MSC-derived exosomes.

2. The vaginal care composition of claim 1, wherein the composition comprises, by weight of the total composition: 5%-40%, 10%-30%, or 15%-25% MSC-derived exosomes.

3. The vaginal care composition of claim 1, wherein the composition comprises, by weight of the total composition: 10%-15%, 15%-20%, or 10%-20% L-carnosine.

4. The vaginal care composition of claim 1, wherein the composition comprises, by weight of the total composition: 25%-50%, 30%-40%, 25%-45%, or 25%-35% magnesium citrate.

5. The vaginal care composition of claim 1, further comprising at least one of the following constituents: *Lactobacillus bifidus, Saccharomyces cerevisiae*, vitamin A, D-alpha-tocopherol, pantothenate, zinc, selenium, or oligofructose.

6. The vaginal care composition of claim 1, further comprising at least one of the following constituents: sunflower oil, Tegomuls 90 S, cetyl alcohol, cetaceum artificiale, Polysorbate 80, methyl 4-hydroxybenzoate, propyl 4-hydroxybenzoate, sesame oil, wool wax, yellow wax, wool wax alcohols, glycerol, glycerol ester, palmitic acid ester, vaseline, cocoa butter, liquid wax, olive oil or distilled water.

7. The vaginal care composition of claim 1, further comprising at least one constituent selected from the group consisting of an antibiotic agent, a free radical generating agent, an antifungal agent, an antiviral agent, a nucleoside-analog reverse transcriptase inhibitor, a non-nucleoside reverse transcriptase inhibitor, a protease inhibitor, an immunosuppressant, an anti-inflammatory agent, a retinoid agent, a tar agent, an antihistamine agent, and an antipruritic agent.

8. A method for improving vaginal health in a subject, comprising administering to the subject in need thereof the vaginal care composition of claim 1.

9. The method of claim 8, wherein the composition comprises, by weight of the total composition: 5%-40%, 10%-30%, or 15%-25% MSC-derived exosomes.

10. The method of claim 8, wherein the composition comprises, by weight of the total composition: 10%-15%, 15%-20%, or 10%-20% L-carnosine.

11. The method of claim 8, wherein the composition comprises, by weight of the total composition: 25%-50%, 30%-40%, 25%-45%, or 25%-35% magnesium citrate.

12. The method of claim 8, wherein the composition further comprises at least one of the following constituents: *Lactobacillus bifidus, Saccharomyces cerevisiae*, vitamin A, D-alpha-tocopherol, pantothenate, zinc, selenium, or oligofructose.

13. The method of claim 8, wherein the composition further comprises at least one of the following constituents: sunflower oil, Tegomuls 90 S, cetyl alcohol, cetaceum artificiale, polysorbate 80, methyl 4-hydroxybenzoate, propyl 4-hydroxybenzoate, sesame oil, wool wax, yellow wax, wool wax alcohols, glycerol, glycerol ester, palmitic acid ester, vaseline, cocoa butter, liquid wax, olive oil or distilled water.

14. The method of claim 8, wherein the composition further comprises at least one constituent selected from the group consisting of an antibiotic agent, a free radical generating agent, an antifungal agent, an antiviral agent, a nucleoside-analog reverse transcriptase inhibitor, a non-nucleoside reverse transcriptase inhibitor, a protease inhibitor, an immunosuppressant, an anti-inflammatory agent, a retinoid agent, a tar agent, an antihistamine agent, and an antipruritic agent.

15. The method of claim 8, wherein the composition is administered intra-vaginally.

16. The method of claim 8, wherein the composition is administered every hour, every two hours, every three hours, every six hours, every twelve hours, every day, every two days, every three days, every five days, every seven days, every ten days, or every fourteen days.

17. The method of claim 8, wherein the subject has been suffering from at least one of the following: vaginal dryness, irritation, dyspareunia, reduced lubrication, post-coital bleeding, decreased arousal, infections, vaginal or pelvic pain.

18. A method for treatment of genitourinary syndrome of menopause (GSM), comprising intra-vaginally administering to a subject in need thereof the vaginal care composition of claim 1.

* * * * *